(12) United States Patent
Sawyer et al.

(10) Patent No.: US 6,664,437 B2
(45) Date of Patent: Dec. 16, 2003

(54) LAYERED COMPOSITES FOR PERSONAL CARE PRODUCTS

(75) Inventors: Lawrence Howell Sawyer, Neenah, WI (US); Andrew Scott Burnes, Medfield, MA (US); Sylvia Bandy Little, Marietta, GA (US); Lisa Ann Schild, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 325 days.

(21) Appl. No.: 09/748,337

(22) Filed: Dec. 21, 2000

(65) Prior Publication Data

US 2002/0120244 A1 Aug. 29, 2002

(51) Int. Cl.$^7$ ................................. A61F 13/15
(52) U.S. Cl. ..................... 604/365; 604/367; 604/374; 604/378
(58) Field of Search ............... 604/365, 367, 604/368, 372, 374, 375, 378; 442/224, 373, 238, 36, 381, 385, 400, 401; 428/172, 212, 219, 297.1, 300.4, 311.51, 311.71

(56) References Cited

U.S. PATENT DOCUMENTS

| | | | |
|---|---|---|---|
| 4,100,324 A | 7/1978 | Anderson et al. | 428/288 |
| 4,340,563 A | 7/1982 | Appel et al. | 264/518 |
| 4,375,448 A | 3/1983 | Appel et al. | 264/518 |
| 4,494,278 A | 1/1985 | Kroyer et al. | 19/304 |
| 4,640,810 A | 2/1987 | Laursen et al. | 264/518 |
| 4,795,668 A | 1/1989 | Krueger et al. | 428/174 |
| 4,818,464 A | 4/1989 | Lau | 264/510 |
| 5,128,082 A | 7/1992 | Makoui | 264/112 |
| 5,277,976 A | 1/1994 | Hogle et al. | 428/397 |
| 5,294,478 A | 3/1994 | Wanek et al. | 428/218 |
| 5,378,528 A | 1/1995 | Makoui | 428/219 |
| 5,432,000 A | 7/1995 | Young, Sr. et al. | 428/372 |
| 5,460,622 A | 10/1995 | Dragoo et al. | 604/378 |
| 5,466,513 A | 11/1995 | Wanek et al. | 428/218 |
| 5,527,171 A | 6/1996 | Soerensen | 425/83.1 |
| 5,549,589 A * | 8/1996 | Horney et al. | 604/366 |
| 5,558,655 A | 9/1996 | Jezzi et al. | 604/378 |
| 5,562,645 A * | 10/1996 | Tanzer et al. | 604/367 |
| 5,601,542 A | 2/1997 | Melius et al. | 604/368 |

(List continued on next page.)

FOREIGN PATENT DOCUMENTS

| | | | |
|---|---|---|---|
| EP | 0 006 647 | 1/1980 | A61F/13/20 |
| EP | 0 730 438 | 9/1996 | A61F/13/15 |
| WO | 95/07673 | 3/1995 | A61F/13/15 |
| WO | 96/07792 | 3/1996 | D21H/27/42 |
| WO | 98/20821 | 5/1998 | A61F/13/00 |
| WO | 98/24960 | 6/1998 | D04H/1/54 |
| WO | 98/43578 | 10/1998 | A61F/13/15 |
| WO | 99/32165 | 7/1999 | |
| WO | 99/63922 | 12/1999 | A61F/13/15 |
| WO | 99/63923 | 12/1999 | A61F/13/15 |
| WO | 99/63925 | 12/1999 | A61F/13/46 |
| WO | 00/27625 | 5/2000 | B32B/5/16 |
| WO | 00/34567 | 6/2000 | |

*Primary Examiner*—Weilun Lo
*Assistant Examiner*—Jacqueline Stephens
(74) *Attorney, Agent, or Firm*—Steven D. Flack

(57) ABSTRACT

There is provided a new multi-layered fibrous material for use in personal care products. In this material, a layer having a mixture of pulp, superabsorbent and binder is adjacent a layer having a very high superabsorbent concentration. The structure is then compacted to a density of between about 0.1 to 0.3 g/cc. These layered structures have better intake properties than traditionally made competitive materials. These structures surprisingly also have better distribution properties than competitive materials. Such a fibrous material is useful in personal care products, like diapers, training pants, incontinence garments and feminine hygiene products.

20 Claims, 2 Drawing Sheets

U.S. PATENT DOCUMENTS

| | | |
|---|---|---|
| 5,614,570 A | 3/1997 | Hansen et al. ................. 524/13 |
| 5,695,486 A | 12/1997 | Broughton et al. .......... 604/374 |
| 5,730,737 A | 3/1998 | Widlund et al. |
| 5,807,364 A | 9/1998 | Hansen ....................... 604/367 |
| 5,820,973 A | 10/1998 | Dodge, II et al. ........... 428/212 |
| 5,843,063 A | 12/1998 | Anderson et al. ............ 604/378 |
| 5,843,852 A | 12/1998 | Dutkiewicz et al. ......... 442/334 |
| 5,849,000 A | 12/1998 | Anjur et al. ................. 604/367 |
| 5,866,242 A | 2/1999 | Tan et al. .................... 428/219 |
| 5,879,343 A | 3/1999 | Dodge, II et al. ........... 604/378 |
| 5,891,119 A | 4/1999 | Ta et al. |
| 5,916,670 A | 6/1999 | Tan et al. .................... 428/219 |
| 5,989,688 A | 11/1999 | Barge et al. ................. 428/198 |
| 6,152,904 A * | 11/2000 | Matthews et al. ........... 604/378 |
| 6,372,953 B1 * | 4/2002 | Young et al. ................ 604/369 |
| 6,503,854 B1 * | 1/2003 | Abuto et al. ................ 442/149 |
| 6,525,240 B1 * | 2/2003 | Graef et al. ................. 604/383 |

* cited by examiner

LAYERED COMPOSITES FOR PERSONAL CARE PRODUCTS

BACKGROUND OF THE INVENTION

The present invention concerns formed materials mainly for personal care products like diapers, training pants, swim wear, absorbent underpants, adult incontinence products and feminine hygiene products. This material may also be useful for other applications such as, for example, in bandages and wound dressings, nursing pads and in veterinary and mortuary applications.

Personal care articles usually have multiple layers of material of some sort to absorb liquids from the body. These layers may include natural fibers, synthetic fibers and superabsorbent particles in varying proportions. When liquid such as urine is deposited into a personal care product like a diaper, it goes through the uppermost layers, typically a liner against the body and a "surge" or "intake" layer designed to provide temporary liquid holding capacity. The product may also have a "distribution" layer designed to move liquid in the X and Y directions in order to utilize more of the absorbent core. After going through these upper layers, the urine enters the absorbent core portion of the product. The absorbent core permanently retains the liquid.

The functions of the layers mentioned above may each be performed by different layers or a layer may perform more than one function. The combination of more than one function in a single layer, however, generally results in a significant decrease in the performance of each of the functions.

Absorbent cores are typically composed of superabsorbent particles and/or pulp. A newer class of absorbents also uses a binder to improve wet stability and to ease converting into final products. Binders can be liquid adhesive or thermally activatable fibers typically present in amounts between 10 and 25 weight percent.

Superabsorbent particles absorb many times their weight in liquid and swell greatly as a result of being wetted. This swelling holds liquid within the product and so protects the wearer's skin, clothing and bedding, but may also block the further intake of liquid. This occurs because the swollen particles become so large as to close off fluid entrances to the structure, a phenomenon known in the art as "gel blocking".

Alternatively, an absorbent structure lacking superabsorbent and made of the traditional pulp and binder fiber can experience "wet collapse". This occurs as a result of saturation of the pulp and the subsequent inability to regenerate void space as fluid is added to the structure. The binder fibers, generally synthetic polymer fibers that are naturally hydrophobic, contribute to this problem since they interfere with the wicking performance of the structure due to their poor wettability. In addition, the constraints induced by the bonding of the binder fibers restrains expansion of the absorbent structure, further reducing void volume and decreasing the ultimate capacity of the material. If the structure were able to wick fluid away from the area of incipient wet collapse more efficiently, the phenomenon might be avoided completely.

A material which treads the fine line between wet collapse and gel blocking would be very desirable. Such a material would avoid the undesirable features of uncontrolled superabsorbent expansion while efficiently absorbing fluids. It would also avoid wet collapse by maintaining a sufficient pore structure, allowing liquid to continue moving through it. Such a material would exhibit high levels of multifunctional absorbent performance.

SUMMARY OF THE INVENTION

In response to the discussed difficulties and problems encountered in the prior art, a new structural composite comprising integrated layers for use in personal care products has been developed. In this material, at least one layer having a mixture of pulp, superabsorbent in an amount between 1 and 30 weight percent and binder in an amount between 1 and 6 weight percent, is adjacent a layer having a very high superabsorbent concentration. There may be alternating layers of similar composition. The overall amount of binder within the structure is at most 4 weight percent and the overall amount of superabsorbent within the structure is between 35 and 80 weight percent. The structure is then compacted to a density of between about 0.1 to 0.3 g/cc. These layered structures have better intake properties than traditionally made competitive materials. These structures surprisingly also have better distribution properties than competitive materials, presumably due to the avoidance of gel blocking, capillary disruption and wet collapse.

Another way of describing this material is as having from two to nine alternating A and B layers where the A layers are a mixture of pulp, binder in an amount between 1 and 6 weight percent and superabsorbent in an amount between 1 and 30 weight percent, and the B layers haver a superabsorbent concentration of at least 80 weight percent. The overall material also has binder in an amount of at most 4 weight percent and superabsorbent in an amount between 35 and 80 weight percent, is compacted to a density of between about 0.1 to 0.3 g/cc and has a basis weight between 80 and 1200 gsm.

The amount of superabsorbent in the A layer is more particularly between 5 and 28 weight percent and still more particularly between 15 and 25 weight percent.

The layered material may have an even number of layers or an odd number of layers. If the layered material has an odd number of layers the outermost layers may be A or B layers. More particular embodiments of the layered material may have 5 layers and a basis weight between 200 and 667 gsm and 7 layers and a basis weight between 280 and 934 gsm.

These materials are suitable for use in personal care products like diapers, training pants, incontinence products, bandages, and sanitary napkins.

DEFINITIONS

Figure 1A:
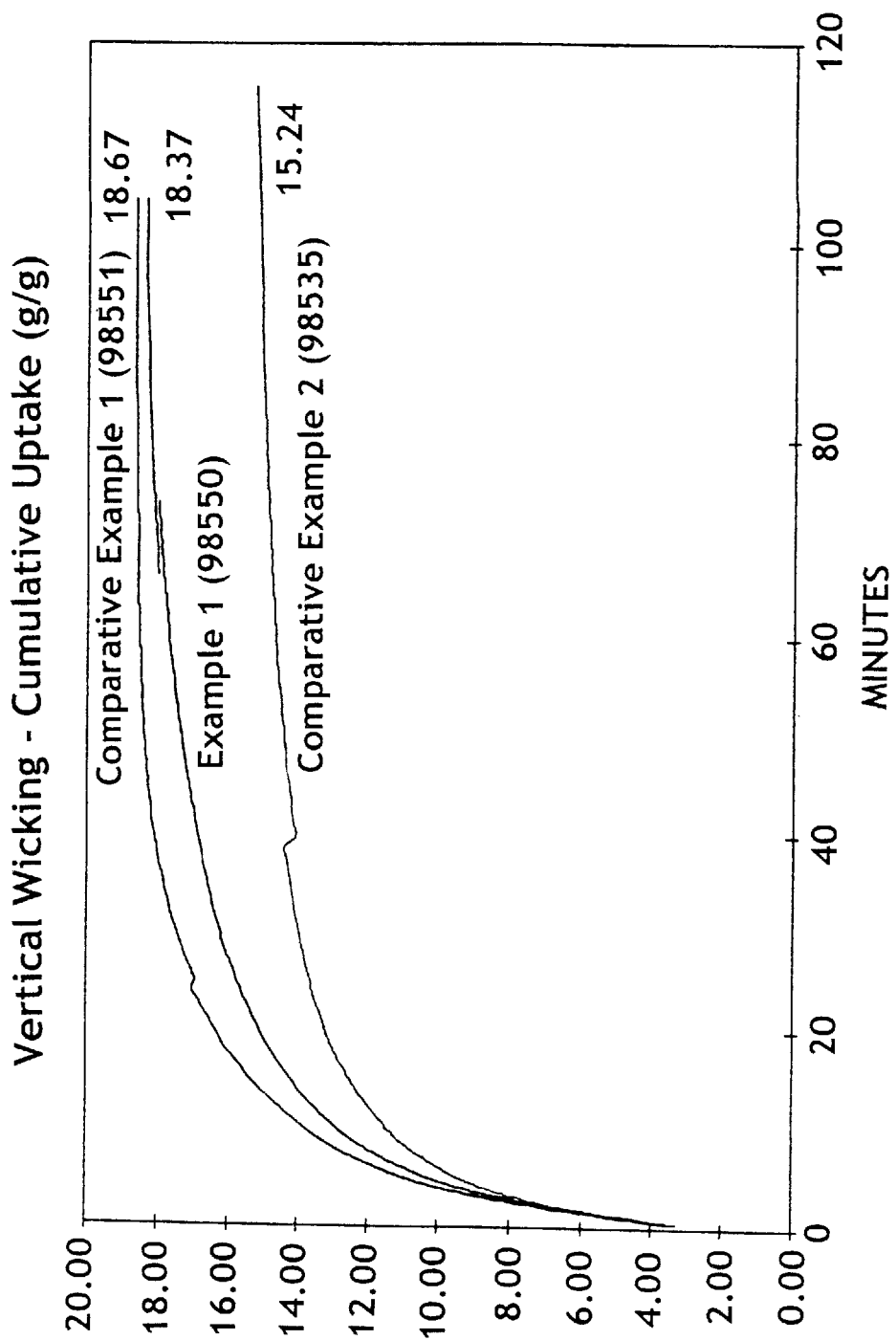
FIG. 1a shows the cumulative uptake of fluid in g/g in a vertical wicking test.

"Liquid communication" means that liquid is able to travel from one layer to another layer, or one location to another within a layer.

"Hydrophilic" describes fibers or the surfaces of fibers that are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials can be provided by a Cahn SFA-222 Surface Force Analyzer System, or a substantially equivalent system. When measured with this system, fibers having contact angles less than 90° are designated "wettable" or hydrophilic, while fibers having contact angles equal to or greater than to 90° are designated "nonwettable" or hydrophobic.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

"Spunbonded fibers" refers to small diameter fibers that are formed by extruding molten thermoplastic material as filaments from a plurality of fine capillaries of a spinneret. Such a process is disclosed in, for example, U.S. Pat. No. 4,340,563 to Appel et al. The fibers may also have shapes such as those described, for example, in U.S. Pat. 5,277,976 to Hogle et al. which describes fibers with unconventional shapes.

"Bonded carded web" refers to webs that are made from staple fibers which are sent through a combing or carding unit, which separates or breaks apart and aligns the staple fibers in the machine direction to form a generally machine direction-oriented fibrous nonwoven web. This material may be bonded together by methods that include point bonding, through air bonding, ultrasonic bonding, adhesive bonding, etc.

As used herein, the term "coform" means a process in which at least one meltblown diehead is arranged near a chute through which other materials are added to the web while it is forming. Such other materials may be pulp, superabsorbent particles, natural fibers (for example, rayon or cotton fibers) and/or synthetic fibers (for example, polypropylene or polyester) fibers, for example, where the fibers may be short cut of staple length. Coform processes are shown in commonly assigned U.S. No, Pat. 4,818,464 to Lau and U.S. Pat. No. 4,100,324 to Anderson et al. Webs produced by the coform process are generally referred to as coform materials.

"Airlaying" is a well-known process by which a fibrous nonwoven layer can be formed.

In the airlaying process, bundles of small fibers having typical lengths ranging from about 3 to about 52 millimeters (mm) are separated and entrained in an air supply and then deposited onto a forming screen, usually with the assistance of a vacuum supply. The randomly deposited fibers then are bonded to one another using, for example, hot air to activate a binder component or a latex adhesive. Airlaying is taught in, for example, U.S. Pat. No. 4,640,810 to Laursen et al.

"Personal care product" means diapers, training pants, swim wear, absorbent underpants, adult incontinence products, bandages and feminine hygiene products. It may further encompass veterinary and mortuary products.

Test Methods and Materials

Basis Weight: A circular sample of 3 inches (7.6 cm) diameter is cut and weighed using a balance. Weight is recorded in grams. The weight is divided by the sample area. Five samples are measured and averaged.

Material caliper or bulk (thickness): The caliper of a material is a measure of thickness and is measured at 0.05 psi (3.5 g/cm$^2$) with a STARRET® bulk tester, in units of millimeters. Samples are cut into 4 inch by 4 inch (10.2 cm by 10.2 cm) squares and five samples are tested and the results averaged.

Density: The density of the materials is calculated by dividing the weight per unit area of a sample in grams per square meter (gsm) by the material caliper in millimeters (mm). The caliper should be measured at 0.05 psi (3.5 g/cm$^2$) as mentioned above. The result is multiplied by 0.001 to convert the value to grams per cubic centimeter (g/cc). A total of five samples would be evaluated and averaged for the density values.

Vertical wicking: A "near" equilibrium test was developed to assess the maximum wicking potential of absorbent composite materials. Many of these composites contain superabsorbent so the approach to equilibrium required more time than non-superabsorbent containing materials, however, it was desired to keep test times within practical lab and use evaluation time frames. A series of experiments with several types of absorbent composites established two hours as the time allowed for materials to achieve "near' liquid saturation profiles for this vertical wicking test.

Test samples were cut in strips 5.08 cm by 17.78 cm. Three samples of each test material were run. The samples were suspended from the bottom sensing element of a Mettler Model 4800 balance and the bottom two centimeters of each sample were submerged in a large 10 weight percent saline reservoir for 120 minutes. Weight pickup was automatically recorded throughout the time period and the whole system was enclosed to minimize air drafts and evaporation. After 120 minutes, the samples were x-rayed to determine the liquid saturation on the material above the submersion line. All g/g values were calculated using the dry and wet mass of the sample above the submersion line.

Void Volume: Void volume of airlaid composites was evaluated at 0, 2.5, 5, 7.5, 10, 15, and 20 g/g saturation levels to determine the amount of void space generated at different levels of saturation. The procedure involves evenly saturating pre-weighed and pre-bulked 3 inch (7.12 cm) round samples to the various saturation levels. The samples are placed in a petri dish with water and left for approximately 20 minutes to allow swelling of the superabsorbent component of the composite. The samples are then removed from the dish, and wet weights and bulks are recorded. The weight of fluid (g) added to a sample is calculated by multiplying the sample dry weight (g) by the saturation level (g'g). Void volume is calculated and reported in cc/g. Three repetitions per sample at each saturation level were performed. These values may be plotted versus the saturation level of the composite. Void volume (cc/g) is calculated as follows:

$$\text{VoidVolume} = \left(\frac{1}{\text{DryWt.}}\right) \times \left[(4.56 * \text{WetBulk}) - \text{DryWt.} * \left(\frac{\% \text{ SAP}}{140} + \frac{\% \text{ Pulp}}{\text{DensityPulp} * 100} + \frac{\% \text{ Binder}}{\text{DensityBinder} * 100} - 1\right) - \text{WetWt.}\right]$$

FIFE: The horizontal Fluid Intake and Flowback Evaluation (FIFE) was performed on all samples to determine the intake potential of the composites. The FIFE entails insulting the structure by pouring a defined amount of 0.9 percent saline solution into a cylindrical column resting vertically on top of the structure and recording the time it takes for the fluid to be taken in by the structure. The sample to be tested is placed on a flat surface and the FIFE testing apparatus placed on top of the sample. The FIFE testing apparatus consisted of a rectangular, 43.2 by 23 cm, gel filled flat piece upon which was centered a cylinder with an inside diameter of 25.4 mm. The flat piece had a 25.4 mm hole corresponding with the cylinder so that fluid could pass through it from the cylinder to the sample. The FIFE testing apparatus weighed 4.63 kg (10.2 pounds).

Intake times are typically recorded in seconds, but, in this case, were recorded as seconds per basis weight. Samples were cut into 6 by 14 inch (15.2 by 35.6 cm) pledgets and were insulted three times at 60 mL per insult with a wait of 15 minutes between the time the fluid was completely absorbed and the next insult.

After the third insult, the materials were placed on a vacuum box under 0.5 psi of pressure with a piece of blotter paper on top. The blotter paper was 110 lb. Verigood paper made by Fort James Corporation and was 3.5 by 12 inches (8.9 by 30.5 cm). The blotter paper was weighed before and after the test and the resulting differential reported as the flowback value as grams of fluid desorbed.

DETAILED DESCRIPTION OF THE INVENTION

This invention relates to a high absorbency, integrated, layered structure of material for personal care products.

The structure has at least two layers. The first layer is made from pulp, superabsorbent and binder. The second layer is made primarily from superabsorbent. Additional layers of either type may be added to the structure.

The first layer has pulp, between 1 and 30 weight percent superabsorbent, and from 1 to 6 weight percent of a binder. The binder may more particularly be between 1 and 5 percent and still more particularly between 1 and 4 percent. The purpose of the binder is to give the structure integrity by binding the fibers and particles together.

The second layer can have between 80 and 100 weight percent superabsorbent preferably between 90 and 100 percent superabsorbent, with a minor amount of pulp and binder.

The overall amount of binder in the structure is at most 4 weight percent and the overall amount of superabsorbent in the structure is between 35 and 80 weight percent.

The absorbent composites and absorbent systems of this invention may be made from a variety of processes traditionally used to prepare stabilized nonwoven webs including coform, carding, meltblowing, spunbonded, airlaying, needlepunching, wetlaying, hydroentangling etc. Preferred embodiments of this application are prepared using the airlaid process. The nonwoven airlaid composites may be prepared from a variety of fibers and mixtures of fibers including but not limited to synthetic fibers, natural fibers including hydroentangled pulp, mechanically and chemically softened pulp, staple fibers, slivers, meltblown and spunbond fibers and the like.

The production of airlaid nonwoven composites is well defined in the literature and documented in the art. Example include the DanWeb process as described in U.S. Pat. No. 5 4,640,810 Laursen et al assigned to Scan Web of North America Inc; the Kroyer process as described in U.S. Pat. No. 4,494,278 Kroyer et al and U.S. Pat. No. 5,527,171 Soerensen assigned to Niro Separation a/s; the method of U.S. Pat. No. 4,375,448 Appel et al assigned to Kimberly-Clark Corporation, or other similar methods. The webs produce by these methods are subsequently bonded together to form an adequate tensile strength web by thermal fusing, latex bonding or combinations thereof, which are well known in the art. Webs produced in this text are best exemplified but not limited to the Danweb process.

Superabsorbents that are useful in the present inventions can be chosen from classes based on chemical structure as well as physical form. These include superabsorbents with low gel strength, high gel strength, surface cross-linked superabsorbents, uniformly cross-linked superabsorbents, or superabsorbents with varied cross-link density throughout the structure. Superabsorbents may be based on chemistries that include poly(acrylic acid), poly(iso-butylene-co-maleic anhydride), poly(ethylene oxide), carboxy-methyl cellulose, poly (-vinyl pyrrollidone), and poly(-vinyl alcohol). The superabsorbents may range in swelling rate from slow to fast. The superabsorbents may be in the form of foams, macroporous or microporous particles or fibers, particles or fibers with fibrous or particulate coatings or morphology. The superabsorbents may be in the shape of ribbons, particles, fibers, sheets or films. Superabsorbents may be in various length and diameter sizes and distributions. The superabsorbents may be in various degrees of neutralization. Counter-ions are typically Li, Na, K, Ca.

Materials of this invention may include superabsorbents of the types mentioned above. An exemplary superabsorbent was obtained from Stockhausen, Inc and is designated FAVOR® SXM 880. Another example of these types of superabsorbents may be obtained from the Dow Chemical Company under the name DRYTECH® 2035. An example of fibrous superabsorbents may be obtained from Camelot Technologies, Ltd., of High River, Alberta, Canada and is designated FIBERDRI® 1241. Another Example included in these types of superabsorbents is obtained from Chemtall Inc. of Riceboro, Ga., and is designated FLOSORB 60 LADY®, also known as LADYSORB 60®. Additional types of superabsorbents not listed here which are commonly available and known to those skilled in the art can also be useful in the present inventions.

Binders typically used in these structures help provide mechanical integrity and stabilization. Binders include fiber, liquid or other binder means that may be thermally activated. Preferred fibers for inclusion are those having a relative melting point such as polyolefin fibers. Lower melting point polymers provide the ability to bond the fabric together at fiber cross-over points upon the application of heat. In addition, fibers having a lower melting polymer, like conjugate and biconstituent fibers are suitable for practice of this invention. Fibers having a lower melting polymer are generally referred to as "fusible fibers". By "lower melting polymers" what is meant are those having a glass transition temperature less than about 175 C. It should be noted that the texture of the absorbent web can be modified from soft to stiff through selection of the fusion and quenching behavior of the polymer. Exemplary binder fibers include conjugate fibers of polyolefins, polyamides and polyesters. Three suitable binder fibers are sheath core conjugate fibers available from KoSa Inc. (Charlotte, N.C.) under the designation T-255 and T-256, both with a polyolefin sheath, or T-254, which has a low melt co-polyester sheath. Many suitable binder fibers are known to those skilled in the art, and are available by many manufacturers such as Chisso and Fibervisions LLC of Wilmington, Del. A suitable liquid binder is KYMENE® 557LX available from Hercules Inc. of Wilmington, Del. Other suitable liquid binders include ethylene vinyl acetate emulsion polymers sold by National Starch and Chemical Company (Bridgewater, N.J.) under the tradename DUR-O-SET® ELITE® series (including ELITE® 33 and ELITE® 22). Other suitable binders are sold by Air Products Polymers and Chemicals under the name AIRFLEX®.

Synthetic fibers include those made from polyolefins, polyamides, polyesters, rayon, acrylics, superabsorbents, TENCEL® regenerated cellulose and any other suitable synthetic fibers known to those skilled in the art. Synthetic fibers may also include kosmotropes for product degradation.

Many polyolefins are available for fiber production, for example polyethylenes such as Dow Chemical's ASPUN® 6811A linear low density polyethylene, 2553 LLDPE and 25355 and 12350 high density polyethylene are such suitable polymers. The polyethylenes have melt flow rates, respectively, of about 26, 40, 25 and 12. Fiber forming polypropylenes include Exxon Chemical Company's ESCORENE® PD 3445 polypropylene and Montell Chemical Co.'s PF304. Many other polyolefins are also available.

Natural fibers include wool, cotton, flax, hemp and wood pulp. Wood pulps include standard softwood fluffing grade such as NB-416 (Weyerhaeuser Corporation, Tacoma, Wash.) and CR-1654 (US Alliance Pulp Mills, Coosa, Ala.). Pulp may be modified in order to enhance the inherent characteristics of the fibers and their processability. Curl may be imparted to the fibers by methods including chemical treatment or mechanical twisting. Curl is typically imparted before crosslinking or stiffening. Pulps may be stiffened by the use of crosslinking agents such as formaldehyde or its derivatives, glutaraldehyde, epichlorohydrin, methylolated compounds such as urea or urea derivatives, dialdehydes such as maleic anhydride, non-methylolated urea derivatives, citric acid or other polycarboxylic acids. Some of these agents are less preferable than others due to environmental and health concerns. Pulp may also be stiffened by the use of heat or caustic treatments such as mercerization. Examples of these types of fibers include NHB416 which is a chemically crosslinked southern softwood pulp fibers which enhances wet modulus, available from the Weyerhaeuser Corporation of Tacoma, Wash. Other useful pulps are debonded pulp (NF405) also from Weyerhaeuser. HPZ3 from Buckeye Technologies, Inc of Memphis, Tenn., has a chemical treatment that sets in a curl and twist, in addition to imparting added dry and wet stiffness and resilience to the fiber. Another suitable pulp is Buckeye HPF2 pulp and still another is IP SUPERSOFT® from International Paper Corporation. Suitable rayon fibers are 1.5 denier Merge 18453 fibers from Tencel Incorporated of Axis, Ala.

An Example and Comparative Examples, all made by the airlaying process, follow:

Example 1 (98550)

An integrated five layered structure was made having alternating layers of superabsorbent and a mixture of superabsorbent, pulp and binder. The first layer (A) towards a wearer was made of 70 weight percent NB416 pulp, 5 weight percent T-255 binder fiber and 25 weight percent FAVOR® SXM 880 superabsorbent and had a basis weight of 115 gsm. The second layer (B) was made of 100 percent FAVOR®) SXM 880 superabsorbent and had a basis weight of 43 gsm. The third layer (C) was identical to layer A. The fourth layer (D) was identical to layer B. The fifth layer (E) was identical to layers A and C. The overall basis weight was 431 gsm, the density was 0.17 g/cm$^3$ and the saturated capacity was 73.9 g/l 100 cm$^2$. The overall structure contained 40 weight percent FAVOR® SXM 880 superabsorbent, 56 weight percent NB416 pulp and 4 weight percent T-255 binder fiber.

Comparative Example 1 (98551)

This is not an example of the invention.

A seven layered (A through G) structure was made having alternating layers of superabsorbent and a mixture of superabsorbent, pulp and binder. The first layer (A) towards a wearer was made of 95 weight percent NB416 pulp and 5 weight percent T-255 binder and had a basis weight of 65 gsm. The second layer (B) was made of 100 percent FAVOR®) SXM 880 superabsorbent and had a basis weight of 58 gsm. Layers C, E and G were identical to layer A. Layers D and F were identical to layer B. The overall basis weight was 434 gsm, the density was 0.17 g/cm$^3$ and the saturated capacity was 73.9 g/l 00 cm$^2$. The overall structure had 40 weight percent FAVOR® SXM 880 superabsorbent, 56 weight percent NB416 pulp and 4 weight percent T-255 binder fiber.

Comparative Example 2 (98535)

This is not an example of the invention.

A homogenous structure was made. It was made with 56 weight percent NB416 pulp, 40 weight percent FAVOR® SXM 880 superabsorbent and 4 weight percent T-255 binder fibers. The overall basis weight was 370 gsm, the density was 0.17 g/cm$^3$ and the saturated capacity was 63.2 g/100 cm$^2$.

Figure 1B:
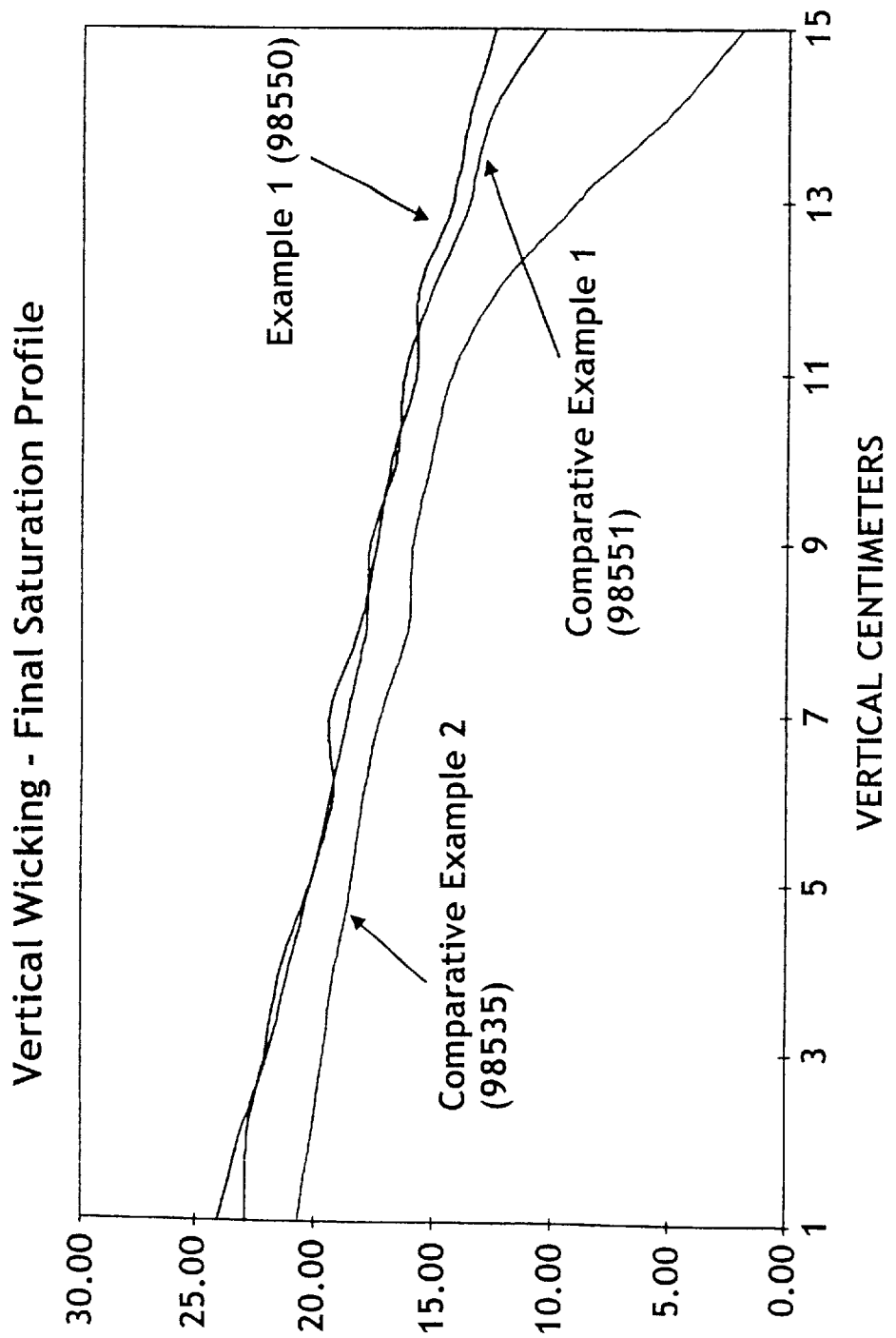
FIG. 1b shows the final saturation profile in a vertical wicking test.

The above materials were tested for vertical wicking, FIFE and void volume. The results for FIFE and void volume are given in Tables 1 and 2 below and the results for vertical wicking given in graphical form in FIGS. 1a and 1b. FIG. 1a shows the cumulative uptake of fluid in g/g with the X-axis denoting minutes and the Y-axis denoting the g/g of fluid. In FIG. 1a, the uppermost line is Comparative Example 1, the middle line is Example 1, and the lowermost line is Comparative Example 2. FIG. 1b shows the final saturation profile with vertical centimeters of fluid movement on the X-axis denoting minutes and the Y-axis denoting the g/g of fluid. In FIG. 1b, the lowermost line is Comparative Example 2, the middle line on the far right is Comparative Example 1 and the uppermost line on the far right is Example 1.

TABLE 1

FIFE results

|  | Code # | 1$^{st}$ Insult (sec/gsm) | 2nd Insult (sec/gsm) | 3rd Insult (sec/gsm) | Flowback (g) |
|---|---|---|---|---|---|
| Example 1. | 98550 | 0.06 | 0.20 | 0.27 | 14.7 |
| Comparative Example 1. | 98551 | 0.08 | 0.21 | 0.31 | 13.0 |
| Comparative Example 2. | 98535 | 0.09 | 0.28 | 0.39 | 17.9 |

TABLE 2

| Saturation Level (g/g) | Void Volume (cc/g) | | | | | | |
|---|---|---|---|---|---|---|---|
| | 0 | 2.5 | 5 | 7.5 | 10 | 15 | 20 |
| Example 1. (98550) | 5.43 | 7.87 | 7.85 | 9.15 | 7.35 | 4.44 | 1.51 |
| Comparative Example 1. (98551) | 4.96 | 6.83 | 7.36 | 6.81 | 6.81 | 4.11 | 2.31 |
| Comparative Example 2. (98535) | 7.36 | 10.06 | 9.2 | 7.83 | 7.39 | 4.35 | 2.7 |

As will be appreciated by those skilled in the art, changes and variations to the invention are considered to be within the ability of those skilled in the art. Examples of such changes and variations are contained in the patents identified above, each of which is incorporated herein by reference in its entirety to the extent consistent with this specification. Such changes and variations are intended by the inventors to be within the scope of the invention.

What is claimed is:

1. A composite layered material for personal care products comprising a first layer which is a mixture of pulp, binder in an amount between 1 and 6 weight percent and superabsorbent in an amount between 1 and 30 weight percent, adjacent a second layer having a superabsorbent concentration of at least 80 weight percent, wherein said composite layered material has binder in an overall amount of at most 4 weight percent and superabsorbent in an overall amount between 35 and 80 weight percent and is compacted to a density of between about 0.1 to 0.3 g/cc.

2. The material of claim 1 wherein said superabsorbent concentration in said second layer is at least 90 weight percent.

3. The material of claim 1 further comprising a third layer adjacent said second layer having a mixture of pulp, binder in an amount between 1 and 6 weight percent and superabsorbent in an amount between 1 and 30 weight percent.

4. The material of claim 3 further comprising a fourth layer adjacent said third layer having a superabsorbent concentration of at least 80 weight percent.

5. The material of claim 4 further comprising a fifth layer adjacent said fourth layer having a mixture of pulp, binder in an amount between 1 and 6 weight percent.

6. A diaper comprising the material of claim 1.

7. A training pant comprising the material of claim 1.

8. An incontinence product comprising the material of claim 1.

9. A bandage comprising the material of claim 1.

10. A sanitary napkin comprising the material of claim 1.

11. A composite layered material for personal care products comprising from two to nine alternating A and B layers, said A layer is a mixture of pulp, binder in an amount between 1 and 6 weight percent and superabsorbent in an amount between 1 and 30 weight percent, and said B layer has a superabsorbent concentration of at least 80 weight percent, wherein said composite layered material has binder in an overall amount of at most 4 weight percent and superabsorbent in an overall amount between 35 and 80 weight percent, is compacted to a density of between about 0.1 to 0.3 g/cc and has a basis weight between 80 and 1200 gsm.

12. The layered material of claim 11 having between 5 and 28 weight percent superabsorbent in said A layer.

13. The layered material of claim 12 having between 15 and 25 weight percent superabsorbent in said A layer.

14. The layered material of claim 11 having an even number of layers.

15. The layered material of claim 11 having an odd number of layers and wherein said outermost layers are A layers.

16. The layered material of claim 11 having an odd number of layers and wherein said outermost layers are B layers.

17. The layered material of claim 15 having 5 layers and a basis weight between 200 and 667 gsm.

18. The layered material of claim 15 having 7 layers and a basis weight between 280 and 934 gsm.

19. The layered material of claim 16 having 5 layers and a basis weight between 200 and 667 gsm.

20. The layered material of claim 16 having 7 layers and a basis weight between 280 and 934 gsm.

* * * * *